United States Patent [19]
Ito et al.

[11] Patent Number: 5,939,433
[45] Date of Patent: *Aug. 17, 1999

[54] QUINUCLIDINE DERIVATIVES

[75] Inventors: Fumitaka Ito, Chita-Taketoyo; Hiroshi Kondo, Handa; Masami Nakane, Showakyu; Kaoru Shimada, Okazaki, all of Japan; John Adams Lowe, III, Stonington, Conn.; Terry Jay Rosen, Burlingame, Calif.

[73] Assignee: Pfizer Inc, New York, N.Y.

[ * ] Notice: This patent issued on a continued prosecution application filed under 37 CFR 1.53(d), and is subject to the twenty year patent term provisions of 35 U.S.C. 154(a)(2).

This patent is subject to a terminal disclaimer.

[21] Appl. No.: 08/846,909

[22] Filed: Apr. 30, 1997

Related U.S. Application Data

[60] Division of application No. 08/211,120, filed as application No. PCT/US92/03317, Apr. 28, 1992, Pat. No. 5,807,867, which is a continuation-in-part of application No. 07/708,404, May 31, 1991, abandoned.

[51] Int. Cl.[6] ..................... C07D 453/00; C07D 453/02; A61K 31/44
[52] U.S. Cl. ............................................. 514/305; 546/133
[58] Field of Search .............................. 514/305; 546/133

[56] References Cited

U.S. PATENT DOCUMENTS

| | | | |
|---|---|---|---|
| 5,714,496 | 2/1998 | Brown et al. | 514/305 |
| 5,716,965 | 2/1998 | Ito et al. | 514/305 |
| 5,744,606 | 4/1998 | Brieden | 546/133 |

*Primary Examiner*—Alan L. Rotman
*Attorney, Agent, or Firm*—Peter C. Richardson; Paul H. Ginsburg; Karen DeBenedicts

[57] ABSTRACT

Compounds of the formula

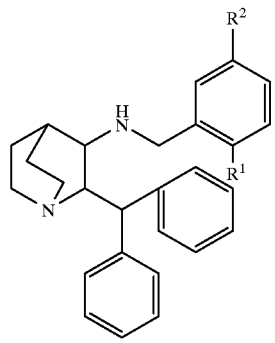

I wherein $R^1$ is methoxy and $R^2$ is selected from the group consisting of methyl, ethyl, isopropyl, sec-butyl and tert-butyl; and the pharmaceutically acceptable salts of such compounds.

These compounds are substance P antagonists and useful in the treatment of gastrointestinal disorders, inflammatory disorders, central nervous system disorders and pain.

3 Claims, No Drawings

QUINUCLIDINE DERIVATIVES

CROSS-REFERENCE

This application is a divisional of Ser. No. 08/211,120 filed on May 23, 1994, U.S. Pat. No. 5,807,867, which is a §371 of PCT/US 92/03317 filed Apr. 28, 1992, which is a C-I-P of Ser. No. 07/708,404 filed May 31, 1991, abandoned.

BACKGROUND OF THE INVENTION

The present invention relates to novel quinuclidine derivatives, pharmaceutical compositions comprising such compounds and the use of such compounds in the treatment and prevention of inflammatory and central nervous system disorders, as well as several other disorders. The pharmaceutically active compounds of this invention are substance P receptor antagonists. This invention also relates to novel intermediates used in the synthesis of such substance P antagonists.

Substance P is a naturally occurring undecapeptide belonging to the tachykinin family of peptides, the latter being named because of their prompt stimulatory action on smooth muscle tissue. More specifically, substance P is a pharmacologically active neuropeptide that is produced in mammals (having originally been isolated from gut) and possesses a characteristic amino acid sequence that is illustrated by D. F. Veber et al. in U.S. Pat. No. 4,680,283. The wide involvement of substance P and other tachykinins in the pathophysiology of numerous diseases has been amply demonstrated in the art. For instance, substance P has recently been shown to be involved in the transmission of pain or migraine (see B. E. B. Sandberg et al., *Journal of Medicinal Chemistry*, 25, 1009 (1982)), as well as in central nervous system disorders such as anxiety and schizophrenia, in respiratory and inflammatory diseases such as asthma and rheumatoid arthritis, respectively, in rheumatic diseases such as fibrositis, and in gastrointestinal disorders and diseases of the GI tract such as ulcerative colitis and Crohn's disease, etc. (see D. Regoli in "Trends in Cluster Headache," edited by F. Sicuteri et al., Elsevier Scientific Publishers, Amsterdam, pp. 85–95 (1987)).

In the recent past, some attempts have been made to provide antagonists for substance P and other tachykinin peptides in order to more effectively treat the various disorders and diseases listed above. The few such antagonists thus far described are generally peptide-like in nature and are therefore too labile from a metabolic point of view to serve as practical therapeutic agents in the treatment of disease. The non-peptidic antagonists of the present invention, on the other hand, do not possess this drawback, being far more stable from a metabolic point of view than the agents referred to above.

The quinuclidine derivatives of this invention are referred to generically in PCT patent application PCT/US 89/05338, filed Nov. 20, 1989 and U.S. Pat. application Ser. No. 557,442, filed Jul. 23, 1990, both of which are assigned in common with the present application. Other quinuclidine derivatives that exhibit activity as substance P receptor antagonists are referred to in PCT patent application PCT/US 91/02853, entitled "3-Amino-2-Aryl Quinuclidines" and filed on Apr. 25, 1991 and in PCT patent application PCT/US 92/03369, entitled "Quinuclidine Derivatives" and filed on May 14, 1991. These applications are also assigned in common with the present application.

Piperidine derivatives and related heterocyclic nitrogen containing compounds that are useful as substance P antagonists are referred to in U.S. Pat. application Ser. No. 619,361, filed Nov. 28, 1990 and U.S. Pat. application Ser. No. 590,423, filed Sep. 28, 1990, both of which are assigned in common with the present application.

SUMMARY OF THE INVENTION

The present invention relates to compounds of the formula

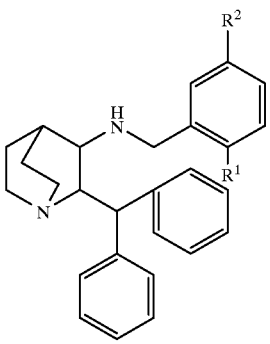

I wherein $R^1$ is methoxy and $R^2$ is independently selected from the group consisting of isopropyl, tert-butyl, methyl, ethyl and sec-butyl; and the pharmaceutically acceptable salts of such compounds.

Specific compounds of this invention include the following:

(2S,3S)-N-(5-isopropyl-2-methoxyphenyl)methyl-2-diphenylmethyl-1-azabicyclo[2.2.2]octan-3-amine;

(2S,3S)-N-(5-tert-butyl-2-methoxyphenyl)methyl-2-diphenylmethyl-1-azabicyclo[2.2.2]octan-3-amine;

(2S,3S)-N-(5-methyl-2-methoxyphenyl)methyl-2-diphenyl-methyl-1-azabicyclo[2.2.2]octan-3-amine;

(2S,3S)-N-(5-ethyl-2-methoxyphenyl)methyl-2-diphenyl-methyl-1-azabicyclo[2.2.2]octan-3-amine;

(2S,3S)-N-(5-isopropyl-2-methoxyphenyl)methyl-2-diphenylmethyl-1-azabicyclo[2.2.2]octan-3-amine;

(2S,3S)-N-(5-sec-butyl-2-methoxyphenyl)methyl-2-diphenylmethyl-1-azabicyclo[2.2.2]octan-3-amine;

and the pharmaceutically acceptable salts of such compounds.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in treating or preventing such condition, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in treating or preventing such condition.

The present invention also relates to a pharmaceutical composition for antagonizing the effects of substance P in a mammal, including a human, comprising a substance P antagonizing amount of a compound of formula I, or a pharmaceutically acceptable salt thereof, and a pharmaceutically acceptable carrier.

The present invention also relates to a method of antagonizing the effects of substance P in a mammal, including a human, comprising administering to said mammal a substance P antagonizing amount of a compound of formula I or a pharmaceutically acceptable salt thereof.

The present invention also relates to a pharmaceutical composition for treating or preventing a disorder in a mammal, including a human, resulting from an excess of substance P, comprising a substance P antagonizing amount of a compound of formula I, or a pharmaceutically acceptable salt thereof, and a pharmaceutically acceptable carrier.

The present invention also relates to a method of treating or preventing a disorder in a mammal, including a human, resulting from an excess of substance P, comprising administering to said mammal a substance P antagonizing amount of a compound of the formula I, or a pharmaceutically acceptable salt thereof.

The present invention also relates to a pharmaceutical composition for treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a condition selected from the group consisting of inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis in a mammal, including a human, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in antagonizing the effect of substance P at its receptor site, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in antagonizing the effect of substance P at its receptor site.

The present invention also relates to a pharmaceutical composition for treating or preventing a disorder in a mammal, including a human, the treatment or prevention of which is effected or facilitated by a decrease in substance P mediated neurotransmission, comprising an amount of a compound of the formula I, or a pharmaceutically acceptable salt thereof, effective in treating or preventing such disorder, and a pharmaceutically acceptable carrier.

The present invention also relates to a method of treating or preventing a disorder in mammal, including a human, the treatment or prevention of which is effected or facilitated by a decrease in substance P mediated neurotransmission, comprising administering to said mammal an amount of a compound of the formula I, or a pharmaceutically acceptable salt thereof, effective in treating or preventing such disorder.

The compounds of this invention, have chiral centers and therefore exist in different enantiomeric forms. This invention relates to all optical isomers and all stereoisomers of compounds of the formula I, and mixtures thereof.

The compounds of this invention include compounds identical to those described above but for the fact that one or more hydrogen, nitrogen or carbon atoms are replaced by isotopes thereof (e.g., tritium or carbon-14 isotopes). Such compounds are useful as research and diagnostic tools in metabolism pharmokinetic studies and in binding assays. Specific applications in research include radioligand binding assays, autoradiography studies and in vivo binding studies, while specific applications in the diagnostic area include studies of the substance P receptor in the human brain in in vivo binding in the relevant tissues for inflammation, e.g.

immune-type cells or cells that are directly involved in inflammatory bowel disorders and the like.

DETAILED DESCRIPTION OF THE INVENTION

The compounds of this invention may be prepared by subjecting a compound of the formula

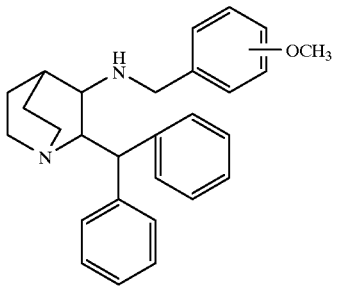

II having the same absolute stereochemistry as the desired compound of formula I, to hydrolytic removal of the methoxybenzyl group to produce the corresponding compound of the formula

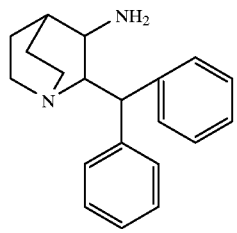

III having the same stereochemistry, and then reacting the compound of formula III so formed with an aldehyde of the formula

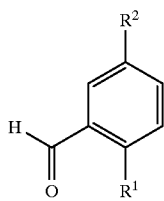

IV in the presence of a reducing agent.

Hydrolytic removal of the methoxybenzyl group is generally carried out using a strong mineral acid such as hydrochloric, hydrobromic or hydroiodic acid, at a temperature from about room temperature to about the reflux temperature of the acid. Preferably, the reaction is conducted in hydrobromic acid at the reflux temperature. This reaction is usually carried out for a period of about 2 hours.

Alternatively, the hydrolytic removal of the methoxybenzyl group in the above procedure may be replaced by hydrogenolytic removal of such group. Hydrogenolytic removal is generally accomplished using hydrogen in the presence of a metal containing catalyst such as platinum or palladium. This reaction is usually conducted in a reaction inert solvent such as acetic acid or a lower alcohol, at a temperature from about 0° C. to about 50° C. The methoxybenzyl group may also be removed, alternatively, by treating the compound of formula II with a dissolving metal such as lithium or sodium in ammonia at a temperature from about −30° C. to about 78° C., or with a formate salt in the presence of palladium or with cyclohexane in the presence of palladium.

Preferably, the methoxybenzyl group is removed by treating the compound of formula II with hydrogen in the presence of palladium hydroxide on carbon in methanol containing hydrochloric acid at a temperature of about 25° C.

The resulting compound of formula III may be converted into the desired compound of formula I by reaction with the appropriate aldehyde of formula IV in the presence of a reducing agent. The reaction is typically carried out using a reducing agent such as sodium cyanoborohydride, sodium triacetoxyborohydride, sodium borohydride, hydrogen and a metal catalyst, zinc and hydrochloric acid, borane dimethylsulfide or formic acid at a temperature from about −60° C. to about 50° C. Suitable reaction inert solvents for this reaction include lower alcohols (e.g., methanol, ethanol and isopropanol), acetic acid, methylene chloride and tetrahydrofuran (THF). Preferably, the solvent is methylene chloride, the temperature is about 25° C., and the reducing agent is sodium triacetoxyborohydride.

Alternatively, the reaction of a compound of the formula III with a compound of the formula IV may be carried out in the presence of a drying agent or using an apparatus designed to remove azeotropically the water generated, to produce an imine of the formula

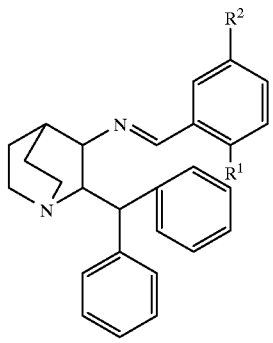

V which is then reacted with a reducing agent as described above, preferably with sodium triacetoxyborohydride at about room temperature. The preparation of the imine is generally carried out in a reaction inert solvent such as benzene, xylene or toluene, preferably toluene, at a temperature from about 25° C. to about 110° C., preferably at about the reflux temperature of the solvent. Suitable drying agents/solvent systems include titanium tetrachloride/dichloromethane, titanium isopropoxide/dichloromethane and molecular sieves/THF. Titanium tetrachloride/dichloromethane is preferred.

Compounds of the formula III may also be converted into compounds of the formula I having the same stereochemistry by reaction with the appropriate compound of the formula

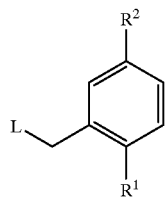

VI wherein L is a leaving group (e.g., chloro, bromo, iodo or mesylate). This reaction is generally carried out in a reaction inert solvent such as dichloromethane or THF, preferably dichloromethane, at a temperature from about 0° C. to about 60° C., preferably at about 25° C.

Compounds of the formula III may also be converted into compounds of the formula I having the same stereochemistry by reacting them with the appropriate compound of the formula

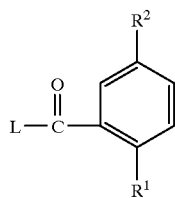

VII wherein L is defined as above or is imidazole, and then reducing the resulting amide. This reaction is typically carried out in an inert solvent such as THF or dichloromethane at a temperature from about −20° C. to about 60° C., preferably in dichloromethane at about 0° C. Reduction of the resulting amide is accomplished by treatment with a reducing agent such as borane dimethylsulfide complex, lithium aluminum hydride or diisobutylaluminum hydride in an inert solvent such as ethyl ether or THF. The reaction temperature may range from about 0° C. to about the reflux temperature of the solvent. Preferably, the reduction is accomplished using borane dimethylsulfide complex in THF at about 60° C.

The novel compounds of the formula I and the pharmaceutically acceptable salts thereof are useful as substance P antagonists, i.e., they possess the ability to antagonize the effects of substance P at its receptor site in mammals, and therefore they are able to function as therapeutic agents in the treatment of the aforementioned disorders and diseases in an afflicted mammal.

The compounds of the formula I which are basic in nature are capable of forming a wide variety of different salts with various inorganic and organic acids. Although such salts must be pharmaceutically acceptable for administration to animals, it is often desirable in practice to initially isolate a compound of the Formula I from the reaction mixture as a pharmaceutically unacceptable salt and then simply convert the latter back to the free base compound by treatment with an alkaline reagent and subsequently convert the latter free base to a pharmaceutically acceptable acid addition salt. The acid addition salts of the base compounds of this invention are readily prepared by treating the base compound with a substantially equivalent amount of the chosen mineral or organic acid in an aqueous solvent medium or in a suitable organic solvent, such as methanol or ethanol. Upon careful evaporation of the solvent, the desired solid salt is readily obtained.

Those compounds of the formula I which are also acidic in nature are capable of forming base salts with various pharmacologically acceptable cations. Examples of such salts include the alkali metal or alkaline-earth metal salts and particularly, the sodium and potassium salts. These salts are all prepared by conventional techniques. The chemical bases which are used as reagents to prepare the pharmaceutically acceptable base salts of this invention are those which form non-toxic base salts with the acidic compounds of formulae I, II and III. Such non-toxic base salts include those derived from such pharmacologically acceptable cations as sodium, potassium calcium and magnesium, etc. These salts can easily be prepared by treating the corresponding acidic compounds with an aqueous solution containing the desired pharmacologically acceptable cations, and then evaporating the resulting solution to dryness, preferably under reduced pressure. Alternatively, they may also be prepared by mixing lower alkanolic solutions of the acidic compounds and the desired alkali metal alkoxide together, and then evaporating the resulting solution to dryness in the same manner as before. In either case, stoichiometric quantities of reagents are preferably employed in order to ensure completeness of reaction and maximum product of yields of the desired final product.

The compounds of Formula I and their pharmaceutically acceptable salts exhibit substance P receptor binding activity and therefore are of value in the treatment and prevention of a wide variety of clinical conditions the treatment or prevention of which are effected or facilitated by a decrease in substance P mediated neurotransmission. Such conditions include inflammatory diseases (e.g., arthritis, psoriasis, asthma and inflammatory bowel disease), anxiety, depression or dysthymic disorders, colitis, psychosis, pain, allergies such as eczema and rhinitis, chronic obstructive airways disease, hypersensitivity disorders such as poison ivy, hypertension, vasospastic diseases such as angina, migraine and Reynaud's disease, fibrosing and collagen diseases such as scleroderma and eosinophilic fascioliasis, reflex sympathetic dystrophy such as shoulder/hand syndrome, addiction disorders such as alcoholism, stress related somatic disorders, peripheral neuropathy, neuralgia, neuropathological disorders such as Alzheimer's disease, AIDS related dementia, diabetic neuropathy and multiple sclerosis, disorders related to immune enhancement or suppression such as systemic lupus erythematosus, and rheumatic diseases such as fibrositis. Hence, these compounds are readily adapted to therapeutic use as substance P antagonists for the control and/or treatment of any of the aforesaid clinical conditions in mammals, including humans.

The compounds of the formula I and the pharmaceutically acceptable salts thereof can be administered via either the oral, parenteral or topical routes. In general, these compounds are most desirably administered in dosages ranging from about 0.5 mg to about 500 mg per day, although variations will necessarily occur depending upon the weight and condition of the subject being treated and the particular route of administration chosen. Variations may occur depending upon the species of animal being treated and its individual response to said medicament, as well as on the type of pharmaceutical formulation chosen and the time period and interval at which such administration is carried out. In some instances, dosage levels below the lower limit of the aforesaid range may be more than adequate, while in other cases still larger doses may be employed without causing any harmful side effect, provided that such larger doses are first divided into several small doses for administration throughout the day.

The compounds of the invention may be administered alone or in combination with pharmaceutically acceptable carriers or diluents by either of the three routes previously indicated, and such administration may be carried out in single or multiple doses. More particularly, the novel therapeutic agents of this invention can be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents, etc. Moreover, oral pharmaceutical compositions can be suitably sweetened and/or flavored. In general, the therapeutically-effective compounds of this invention are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active ingredient may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of a therapeutic compound of the present invention in either sesame or peanut oil or in aqueous propylene glycol may be employed. The aqueous solutions should be suitably buffered (preferably pH greater than 8) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

Additionally, it is also possible to administer the compounds of the present invention topically when treating inflammatory conditions of the skin and this may preferably be done by way of creams, jellies, gels, pastes, ointments and the like, in accordance with standard pharmaceutical practice.

The activity of the compounds of the present invention as substance P antagonists is determined by their ability to inhibit the binding of substance P at its receptor sites in bovine caudate tissue, employing radioactive ligands to visualize the tachykinin receptors by means of autoradiography. The substance P antagonizing activity of the herein described compounds may be evaluated by using the standard assay procedure described by M. A. Cascieri et al., as reported in the *Journal of Biological Chemistry*, Vol. 258, p. 5158 (1983). This method essentially involves determining the concentration of the individual compound required to reduce by 50% the amount of radiolabelled substance P ligands at their receptor sites in said isolated cow tissues, thereby affording characteristic $IC_{50}$ values for each compound tested.

In this procedure, bovine caudate tissue is removed from a −70° C. freezer and homogenized in 50 volumes (w./v.) of an ice-cold 50 mM Tris (i.e., trimethamine which is 2-amino-2-hydroxymethyl-1,3-propanediol) hydrochloride buffer having a pH of 7.7. The homogenate is centrifuged at 30,000×G for a period of 20 minutes. The pellet is resuspended in 50 volumes of Tris buffer, rehomogenized and then recentrifuged at 30,000×G for another twenty-minute period. The pellet is then resuspended in 40 volumes of ice-cold 50 mM Tris buffer (pH 7.7) containing 2 mM of calcium chloride, 2 mM of magnesium chloride, 40 g/ml of bacitracin, 4 µg/ml of leupeptin, 2 µg of chymostatin and 200 g/ml of bovine serum albumin. This step completes the production of the tissue preparation.

The radioligand binding procedure is then carried out in the following manner, viz., by initiating the reaction via the addition of 100 µl of the test compound made up to a concentration of 1 µM, followed by the addition of 100 µl of radioactive ligand made up to a final concentration 0.5 mM and then finally by the addition of 800 µl of the tissue preparation produced as described above. The final volume is thus 1.0 ml, and the reaction mixture is next vortexed and incubated at room temperature (ca. 20° C.) for a period of 20 minutes. The tubes are then filtered using a cell harvester, and the glass fiber filters (Whatman GF/B) are washed four times with 50 mM of Tris buffer (pH 7.7), with the filters having previously been presoaked for a period of two hours prior to the filtering procedure. Radioactivity is then determined in a Beta counter at 53% counting efficiency, and the $IC_{50}$ values are calculated by using standard statistical methods.

The anti-psychotic activity of the compounds of the present invention as neuroleptic agents for the control of various psychotic disorders is determined primarily by a study of their ability to suppress substance P-induced or substance P agonist induced hypermotility in guinea pigs. This study is carried out by first dosing the guinea pigs with a control compound or with an appropriate test compound of the present invention, then injecting the guinea pigs with substance P or a substance P agonist by intracerebral administration via canula and thereafter measuring their individual locomotor response to said stimulus.

The present invention is illustrated by the following examples. It will be understood, however, that the invention is not limited to the specific details of these examples.

EXAMPLE 1

(2S,3S)-N-(5-isopropyl-2-methoxythenyl)methyl-2-diphenylmethyl-1-azabicyclo[2.2.2]octan-3-amine Methanesulfonic Acid Salt A. (2S,3S)-2-(2-diphenylmethyl-1-azabicyclo[2.2.2]-octan-3-amine (2S,3S)-N-(2-methoxyphenyl)methyl-1-azabicyclo[2.2.2]-octan-3-amine (4.12 g, 10 mmol) was hydrogenated at room temperature in methanol (MeOH) (40 ml)/6N hydrochloric acid (HCl) (10 ml) by using 20% palladium hydroxide on carbon (0.2 g) at 2.5 kg/cm² of hydrogen for 60 hours. The reaction was filtered and the filtrate was concentrated to give the crude product, which was crystallized from ethanol.

B. (2S,3S)-N-(5-isopropyl-2-methoxyohenyl)methyl-2-diphenylmethyl-1-azabicyclo[2.2.2]octan-3-amine Methanesulfonic Acid Salt To a solution of a 5-isopropyl-2-methoxybenzaldehyde (748 mg, 4.2 mmol) and (2S,3S)-2-diphenylmethyl-1-azabicyclo[2.2.2]octan-3-amine (4 mmol) in methylene chloride (CH$_2$Cl$_2$) (40 ml) was added in portions triacetoxyborohydride (933 mg, 4.4 mmol). The mixture was stirred until the amine disappeared. The solution was carefully neutralized with an ice-cooled saturated sodium bicarbonate (NaHCO$_3$) solution. The organic layer was washed with water, dried over magnesium sulfate (MgSO$_4$), and concentrated to give the product (1.82 g). To a solution of the product in acetone was added equivalent methansulfonate acid. Then the precipitated mesylate salt was collected and dried under vacuum.

The title compounds of Examples 2–15 were prepared by a procedure similar to that of Example 1.

EXAMPLE 2

(2S,3S)-N-(5-methyl-2-methoxyphenyl)methyl-2-diphenyl-methyl-1-azabicyclo[2.2.2]octan-3-amine Methanesulfonic Acid Salt M.p.: 240° C.

IR (KBr) cm$^{-1}$: 3410, 2980, 1640, 1500, 1455, 1200, 1060, 710.

$^1$H NMR (CDCl$_3$) δ: 7.5–7.2 (10H, m), 7.10 (1H, m) 8.40 (1H, br), 6.63 (1H, d, J=8 Hz), 6.39 (1H, br s), 4.55 (1H, m) 4.12 (1H, m), 3.80–3.30 (5H, m), 3.53 (3H, s), 3.25 (1H, m), 3.20 (1H, m), 2.47 (3H, s), 2.42 (1H, m), 2.21 (3H, s), 2.30–2.16 (4H, m).

EXAMPLE 3

(2S,3S)-N-(5-ethyl-2-methoxyphenyl)methyl-2-diphenylmethyl-1-azabicyclo[2.2.2]octan-3-amine Methanesulfonic Acid Salt M.p.: 151° C.

IR (KBr) cm$^{-1}$: 3420, 2970, 1640, 1510, 1460, 1195, 1060, 785.

$^1$H NMR (CDCl$_3$) δ: 10.9 (1H, br), 8.18 (1H, br) 7.85–7.15 (11H, m), 6.86 (1H, m), 6.68 (1H, d, J=8.8 Hz), 5.57 (1H, br) 5.45 (1H, m) 5.05 (1H, d, J=13.2 Hz), 4.24–3.65 (5H, m), 3.48 (3H, s), 3.50–3.35 (3H, m), 2.92 (1H, m), 2.61 (6H, s), 2.8–2.2 (6H, m), 2.54 (2H, m), 2.30–1.80 (2H, m), 1.21 (3H, m).

EXAMPLE 4

(2S,3S)-N-(5-isopropyl-2-methoxyphenyl)methyl-2-diphenylmethyl-1-azabicyclo[2.2.2]octan-3-amine Methanesulfonic Acid Salt M.p.: 221° C.

IR (KBr) cm$^{-1}$: 3430, 2960, 1600, 1500, 1455, 1245, 1160, 1040, 710.

$^1$H NMR (CDCl$_3$) δ: 8.40 (1H, br) 7.5–7.2 (10H, m) 7.06 (1H, m), 6.67 (1H, d, J=8.4 Hz), 6.56 (1H, br, s) 4.58 (1H, m) 4.24 (1H, m), 3.6–3.3 (5H, m), 3.53 (3H, s), 3.24 (1H, m), 3.22 (1H, m), 2.78 (1H, sep, J=7 Hz), 2.48 (4H, s), 2.42 (1H, m), 2.27 (1H, m), 1.99 (2H, m), 1.76 (1H, m), 1.20 (6H, dd, J=2.9 Hz, 7 Hz).

EXAMPLE 5

(2S,3S)-N-(5-sec-butyl-2-methoxyphenyl)methyl-2-diphenylmethyl-1-azabicyclo[2.2.2]octan-3-amine Methanesulfonic Acid Salt M.p.: 224° C.

IR (KBr) cm$^{-1}$: 3440, 2960, 1610, 1500, 1455, 1220, 1160, 1035, 755, 710, 560.

$^1$H NMR (CDCl$_3$) δ: 8.41 (1H, br), 7.5–7.2 (10H, m) 7.00 (1H, m), 6.67 (1H, d, J=8.4 Hz), 6.52 (1H, br, s) 4.58 (1H, d, J=11.7 Hz), 4.25 (1H, m), 3.70–3.35 (5H, m), 3.53 (3H, s), 3.21 (2H, m), 2.46 (3H, s), 2.43 (1H, m), 2.26 (1H, m), 2.04 (1H, m), 2.00–1.60 (3H, m), 1.52 (2H, m), 1.18 (2H, m), 0.82 (3H, m).

We claim:

1. A method of treating a condition selected from the group consisting of inflammatory diseases, anxiety, colitis, depression or dysthymic disorders, psychosis, pain, allergies, chronic obstructive airways disease, hypersensitivity disorders, hypertension, vasospastic diseases, fibrosing and collagen diseases, reflex sympathetic dystrophy, addiction disorders, stress related somatic disorders, peripheral neuropathy, neuralgia, neuropathological disorders, disorders related to immune enhancement or suppression and rheumatic diseases in a mammal, comprising administering to a mammal in need of such treatment an amount of a compound of the formula

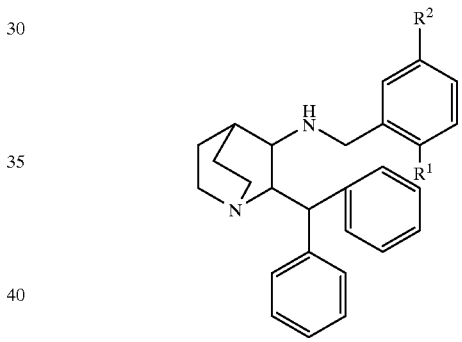

wherein R$^1$ is methoxy and R$^2$ is independently selected from the group consisting of isopropyl, tert-butyl, methyl, ethyl and sec-butyl, or a pharmaceutically acceptable salt of such compound, that is effective in treating such condition.

2. A method of treating a condition in a mammal, the treatment of which is effected or facilitated by a decrease in substance P mediated neurotransmission, comprising administering to a mammal in need of such treatment an amount of a compound according to claim 1, or a pharmaceutically acceptable salt thereof, effective in antagonizing the effect of substance P at its receptor site.

3. A method of treating a condition in mammal, the treatment of which is effected or facilitated by a decrease in substance P mediated neurotransmission, comprising administering to a mammal in need of such treatment an amount of a compound according to claim 1 effective in treating such condition.

* * * * *